(12) United States Patent
Feske

(10) Patent No.: US 6,536,943 B1
(45) Date of Patent: Mar. 25, 2003

(54) METHOD AND APPARATUS FOR TESTING FLAMMABILITY PROPERTIES OF CELLULAR PLASTICS

(75) Inventor: Elbert F. Feske, Denham Springs, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/982,487

(22) Filed: Oct. 17, 2001

(51) Int. Cl.[7] .................... C09K 21/00; G01N 25/00; G01N 17/00
(52) U.S. Cl. ................... 374/8; 374/31; 436/147; 252/607
(58) Field of Search .................. 73/61.76, 61.77; 436/147, 155, 156; 374/8, 29–30, 43–44, 10–11, 31–33; 252/601, 607, 608

(56) References Cited

U.S. PATENT DOCUMENTS

| | | | |
|---|---|---|---|
| 4,112,410 A | 9/1978 | Wrob et al. | 338/243 |
| 4,346,287 A | 8/1982 | Desloge | 219/541 |
| 4,558,210 A | 12/1985 | Leary | 219/535 |
| 5,247,158 A | 9/1993 | Steinhauser et al. | 219/544 |
| 5,864,941 A | 2/1999 | Baichoo et al. | 29/611 |
| 5,902,518 A | 5/1999 | Khazai et al. | 252/511 |
| 5,981,290 A * | 11/1999 | Lyon et al. | 436/157 |
| 6,037,574 A | 3/2000 | Lanham et al. | 219/544 |
| 6,124,579 A | 9/2000 | Steinhauser et al. | 219/544 |
| 6,147,335 A | 11/2000 | Von Arx et al. | 219/544 |
| 6,188,051 B1 | 2/2001 | Kusek | 219/544 |
| 6,200,023 B1 * | 3/2001 | Tay et al. | 374/161 |
| 6,222,166 B1 | 4/2001 | Lin et al. | 219/538 |
| 6,263,158 B1 | 7/2001 | Rutherford | 392/503 |

* cited by examiner

Primary Examiner—Diego Gutierrez
Assistant Examiner—Gail Verbitsky
(74) Attorney, Agent, or Firm—Edgar E. Spielman, Jr.

(57) ABSTRACT

Methods and apparatus for testing flammability properties of cellular plastics are described. Heat is applied to the underside of a heat-conductive plate on which is placed a specimen of the cellular plastic. A plurality of spaced-apart heat sensing devices are positioned below the specimen and in direct or close contact with the plate, one such heat sensing device being centrally positioned relative to the plate and serving as the setpoint sensor. A plurality of spaced-apart heat sensing devices are also disposed above the specimen and in direct or close contact with the top surface of the specimen, one such heat sensing device being centrally positioned relative to the top of the specimen. The sensing devices are adapted to provide signals convertible into information regarding the temperatures at their respective locations. At a preselected elevated temperature as sensed by the setpoint sensor, the time for the sensors on top of the specimen to sense a rise in temperature and/or to reach a preselected temperature is/are measured. Preferably, physical characteristics of the cellular plastic on completion of the test are also inspected.

10 Claims, 5 Drawing Sheets

METHOD AND APPARATUS FOR TESTING FLAMMABILITY PROPERTIES OF CELLULAR PLASTICS

BACKGROUND

Building codes in the United States place certain fire restrictions on cellular plastics used in construction. Sheathing products must at least meet the Class II requirements of the ASTM E-84 test: flame spread $\leq 75$ and smoke $\leq 450$. Class I E-84 criteria ($\leq 25$ flame spread and $\leq 450$ smoke) are desirable, but not specifically called for in the building codes.

Roofing products, in addition to other tests, must meet the Factory Mutual Class I Approval as described in Factory Mutual Procedure 4450/4470. An important component of the Factory Mutual 4450/4470 procedure is the so-called FM Calorimeter test (hereinafter referred to as the context requires as the Calorimeter test, Calorimeter testing, or Calorimeter). In the Factory Mutual (FM) Calorimeter test, a 22.5 ft.$^2$ section of the particular roof construction is subjected to a heptane-fired flame for thirty minutes. According to the FM 4450 standard, the intended sample exposure is 1650 BTU/min./ft.$^2$ The heat release rate and total BTU content of the sample is determined and compared to the acceptance criteria. The FM Calorimeter test reports the peak heat release rates for the worst 3-minute, 5-minute, and 10-minute periods, as determined from the time/temperature curve. The average heat release rate, equal to the sample (total BTU/448), is also reported and used as a pass/fail criteria.

Approvals obtained under FM 4450/4470 are specific to the roof construction tested. The approval is limited to a minimum thickness of the insulation, and to the particular construction. For years, the 'worst case' construction has been the '4-ply glass' built-up roofing (BUR) system. In this construction, the foam insulation is applied directly over a fluted steel roof deck. The steel decking in the test sample is not continuous. It is composed of two pieces, overlapped by about ¼" and not secured with stitch screws. The top surface of the foam insulation is then mopped with Type 3 asphalt. Seven overlapped pieces of glass ply-sheet are applied with alternating moppings of asphalt to secure the ply sheets. A final asphalt mopping or 'flood coat' is then applied to the top surface of the roof deck. Starting in 2001, FM instituted routine weighing of the roof deck to determine the total amount of asphalt applied. The asphalt application rate is reported by FM to be included in any subsequent approvals from the particular sample. Asphalt application rates are critical because our results indicate that there is not enough BTU contribution available from a typical 1.5" PIR foam board to fail the Calorimeter test.

Prior to this invention, the results of Calorimeter testing by others has been made available to see if such information would enable the development of superior test method. Such Calorimeter testing has included diagnostic tests, including the use of test decks using commercially-produced coverboards and no asphalt. Also made available as background information were the results of extensive determinations of the total available BTU content of all roof deck components, using bomb calorimetry. Such data, summarized in Table 1, allows the researcher to calculate the approximate total BTU content of any Calorimeter test deck. The BTU content of each component is shown in BTU/lb. as well as the total pounds and BTU typically installed on the 22.5 ft.$^2$ test deck. The BTU content should be determined for each foam formulation, and for any alteration in type or supply of the deck components.

Also made available was information based on BTU determinations of the char remaining after the Calorimeter test, and calculations of the net BTU consumption in the Calorimeter. It had been found that typically the total BTU content of the deck, as reported by the Calorimeter, is 10–35% higher than the available BTU as determined by the bomb calorimeter, even when it is assumed that the entire 22.5 ft.$^2$ of the Calorimeter test deck is consumed. Actual measurements indicated that approximately 19 ft.$^2$, or 85% of the total Calorimeter test deck area, participates in the test. This is in contrast to the 16 ft.$^2$, or 71%, of the total test deck are assumed in the Calorimeter test procedure and calculations.

Results of, and conclusions from, investigations on the reproducibility of the Calorimeter test were also provided as background information. These investigations had been conducted with repeat tests of the same board in identical constructions. The data indicates that 1 standard deviation for the average BTU/ft.$^2$ min. for a typical '4-ply glass' BUR construction is on the order of 50 BTU/ft.$^2$ min. The 2σ (95%) confidence interval then is 285$^+$/−100 BTU/ft.$^2$ min.

Recent measurements show that temperatures of 1500–1600° F. (820–870 C) can develop on the underside of the steel deck during the Calorimeter test. Similar temperatures have been recorded for research Calorimeter tests, using constructions that employed a cover board and no asphalt. The temperatures recorded as part of the Calorimeter test were measured in the exhaust flue by an array of 12 thermocouples and averaged. Measurements showed that the actual exposure temperature of the test deck can be up to 400° higher. Temperatures are lower in the exhaust flue of the Calorimeter due to mixing of stratified airflow.

Under the test deck exposure conditions, the ideal roof insulating material should provide a thick intumescent char, with minimal cracking, that would protect the asphalt in the BUR test sample. The insulation in the test sample is composed of four separate pieces that are butted together in the form of a square when viewed from above. For this reason, the ideal insulation also will not shrink or contract when exposed to the test conditions. Shrinkage will open up seams at the butt-joints and allow melted asphalt to flow through, eventually reaching the inside of the firebox and contributing to the observed total BTU. Laboratory screening tests focus on three key attributes of the foam: thickness retention, lateral shrinkage, and char integrity.

Several prior laboratory flammability methods are available to the researcher. The most common and easiest screening procedure is the so-called 'hot-plate' test. The roof insulation product is cut to 4"x4" samples and placed on a pre-heated laboratory hotplate. Samples may be from faced production boards or from un-faced laboratory foams. A 900 gram weight maintains contact of the foam on the sample stage and prevents curling. The sample is heated on one side in the same manner as in the Calorimeter. Typically the hotplate is heated to 850° F. and the sample is exposed for 30 minutes. In fact, the temperature should be 870° C. (1598° F.) to simulate the actual exposure in the Calorimeter. Commercially available laboratory hotplates will generally not reach the same temperatures as the Calorimeter. Historically, a hotplate temperature of 800–850° F. has been used and correlated empirically to the Calorimeter.

Prior to October, 1999 this correlation served fairly well. Under the old Calorimeter correlation, results of 15% or less thickness loss in the hotplate are considered good and the material is a good candidate for Calorimeter testing. Results of 16–25% thickness loss in the hotplate are considered marginal candidates for Calorimeter testing. Those boards with >25% thickness loss in the hotplate are generally not considered for Calorimeter testing.

Statistical treatment of hotplate data showed that the 95% confidence limit is fairly broad. For this reason, hotplate data has traditionally been used only as a screening method. In spite of the large error bars associated with hotplate results, trends became obvious when large data sets of similar density foams were compared for different flame retardant combinations.

Weight loss and dimensional change have generally not been used as criteria for hotplate screening of materials for Calorimeter testing. Wide variation in thickness change is seen with samples that have substantially the same weight loss. Dimensional stability has been re-evaluated with regard to Calorimeter performance and the new method of the present invention. Of particular interest is any lateral shrinkage of the foam that will open the main seam in the Calorimeter test and allow molten asphalt to reach the firebox.

After October 1999, experts in this field detected an apparent base-line shift in the Calorimeter. Identical boards from the same bundle were tested in the FM Calorimeter and produced substantially different total BTU results. The total BTU reported by the Calorimeter was approximately 54% higher in the more recent tests (<115,000 vs. >177,000 BTU). This outcome was found with manufactured PIR boards produced both with 141b and hydrocarbon blowing agents. One result of the shift was that a new correlation between the laboratory methods and the Calorimeter had to be established. It was also desirable to develop new laboratory methods that were better predictors of Calorimeter performance.

Accordingly, the provider of the foregoing background information expressed the desire for the development of a new, more definitive laboratory test. A first attempt at fulfilling this desire was a method based on use of a vented oven capable of reaching 1200° F. (650° C.). While giving a good first indication of char formation, concern remained that the method did not offer information on the large-scale cracking behavior of the foam char. In addition, the vented oven exposes the sample to heat on all six sides, unlike the Calorimeter. Thus a need exists for a new test method and new apparatus capable of more accurately predicting how foam test specimens will behave in the required (and expensive) Calorimeter test.

The present invention is deemed to fulfill the foregoing needs and desires in an efficient and effective manner. At the same time it avoids the shortcomings noted for the vented oven test procedure.

SUMMARY OF THE INVENTION

The methods of this invention involve:
a) applying heat to the underside of a heat-conductive plate on which are disposed (i) a test specimen of the cellular plastic having a top surface and a bottom surface, (ii) a plurality of spaced-apart heat sensing devices disposed below the specimen and in direct or substantially direct contact with the plate, one such heat sensing device being substantially centrally disposed relative to the plate and serving as the setpoint sensor, and (iii) a plurality of spaced-apart heat sensing devices disposed above the specimen and in direct or substantially direct contact with the top surface of the specimen, one said heat sensing device being substantially centrally disposed relative to the top surface of the specimen, the sensing devices being adapted to provide signals convertible into information regarding the temperatures at their respective locations; and
b) at a preselected elevated temperature as sensed by said setpoint sensor, determining the time for the sensors of (iii) to sense a rise in temperature and/or to reach a preselected temperature at or below the preselected elevated temperature sensed by said setpoint sensor.

Apparatus of this invention comprises:
a) a heat-conductive plate having upper and lower surfaces, each surface having a central location;
b) a heater centrally or substantially centrally disposed relative to said central locations of the plate;
c) a plurality of heat sensing devices adapted, when a specimen of a cellular plastic is placed on said plate, to be disposed in spaced-apart locations below the test specimen and in direct or substantially direct contact with the plate and to transmit signals convertible into information regarding the temperature at the location of the heat sensing device;
d) a plurality of spaced-apart heat sensing devices adapted, when a specimen of a cellular plastic is placed on said plate, to be disposed in spaced apart locations above the specimen and in direct or substantially direct contact with a top surface of the specimen, and to transmit signals convertible into information regarding the temperature at the location of the heat sensing device;
e) a thermally insulated housing including a thermally insulated cover, said housing and said cover when closed being adapted to encase said plate, a specimen of a cellular plastic when placed on said plate, and said heater entirely or substantially entirely within the confines of said housing and cover;
f) a microprocessor adapted to receive signals from the respective heat sensing devices, and to convert said signals into signals corresponding to temperatures sensed by the respective sensing devices; and
g) a display device, adapted to receive the signals from said microprocessor and to display information indicative of the respective temperatures sensed by the respective sensing devices;

wherein f) and g) can be separate units or a single combined unit.

The heater used is preferably a thermally insulated radiant heater capable of heating test samples through the plate to temperatures of up to about 870° C. (1600° F.) or higher, temperatures which are not achievable by use of conventional hot plates.

Other embodiments and features of this invention will be still further apparent from the ensuing description, the accompanying drawings, and the appended claims.

BRIEF DESCRIPTION OF THE DRAWINGS

In the Drawings like numerals represent like elements among the various views depicted.

FURTHER DETAILED DESCRIPTION OF THE INVENTION

Figure 1:
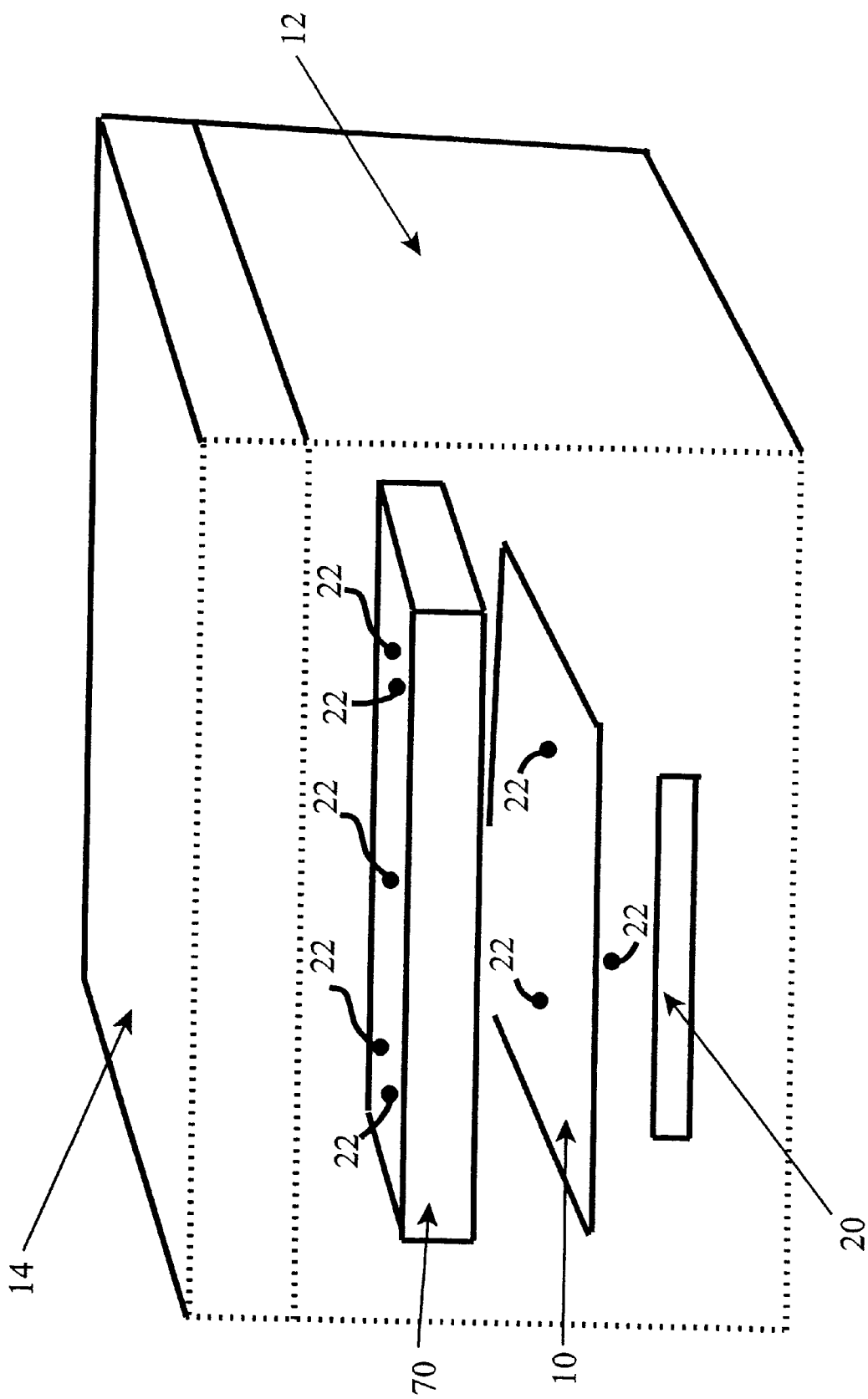
FIG. 1 is a schematic exploded frontal perspective view in section of components of a testing device of this invention.

In the schematic exploded form illustrated in FIG. 1, the apparatus includes plate 10 on which a test specimen 70 (e.g., a 2'×2' plastic foam panel) is placed for a test. A heater 20 is disposed, preferably centrally disposed, underplate 10. The apparatus typically includes a thermally insulated enclosure 12 which includes a hinged thermally insulated lid 14 which when closed encases all of the foregoing components including the test specimen.

Although plate 10 can be of various configurations in plan view, such as circular or rectangular, preferably it is square in plan view. As used herein, "square", "rectangular", "triangular", "circular" and "pie-shaped" in connection with shapes of the plate or of test specimens or pieces thereof refers to shapes in plan view only.

Test specimen 70 is instrumented with a plurality of heat sensing devices 22 which are adapted to furnish signals to a converter/recorder so that a continuous record of the temperatures at the sites of the temperature sensing devices as these temperatures progressively increase during the test is developed and maintained. The number of heat sensing devices 22 and the patterns in which they can be arranged are virtually unlimited, provided only that one such heat sensing device is substantially centrally disposed above plate 10 and below test specimen 70. Preferably another such heat sensing device is substantially centrally disposed above, and most preferably either in direct contact with, or within a few millimeters above, test specimen 70.

Figure 2:
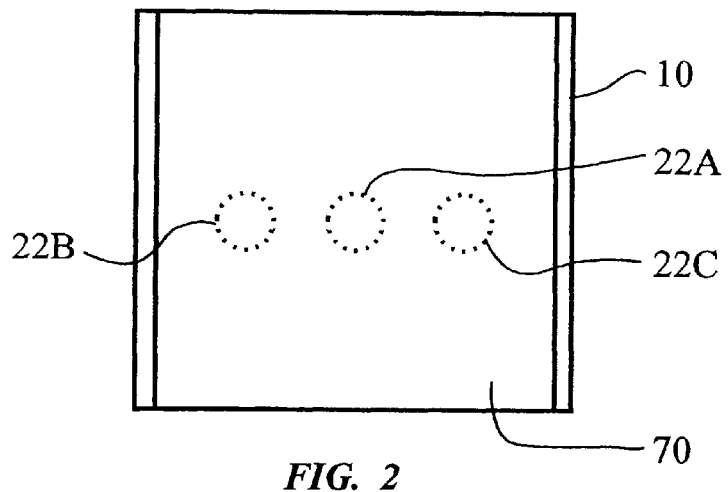
FIG. 2 is a schematic plan view of a testing device of this invention illustrating one pattern for the disposition of a plurality of heat sensing devices underneath a test specimen.

FIG. 2 depicts one preferred pattern for the disposition of heat sensing devices 22 beneath test specimen 70 and above plate 10 which has been found in practice to provide the necessary temperature input data to the specimen and yet to require only three heat sensing devices. It will be seen from FIG. 2 that heat sensing device 22A is substantially centrally disposed above plate 10 and below test specimen 70 (depicted by phantom lines in FIG. 2). Temperature readings from heat sensing device 22A serves as the control or set-point temperatures. The other two heat sensing devices 22B and 22C are laterally spaced apart from heat sensing device 22A so that they are substantially equidistant from heat sensing device 22A, yet are still within the perimeter of the area occupied by test specimen 70 atop plate 10. Readings from heat sensing devices 22B and 22C serve to indicate the lateral temperature profile across plate 10 as heat from the plate is lost to the exterior surroundings. If desired, more than three such heat sensing devices can be used for this purpose. It may also be possible to use less than three heat such sensing devices, but this is not recommended.

Figure 3:
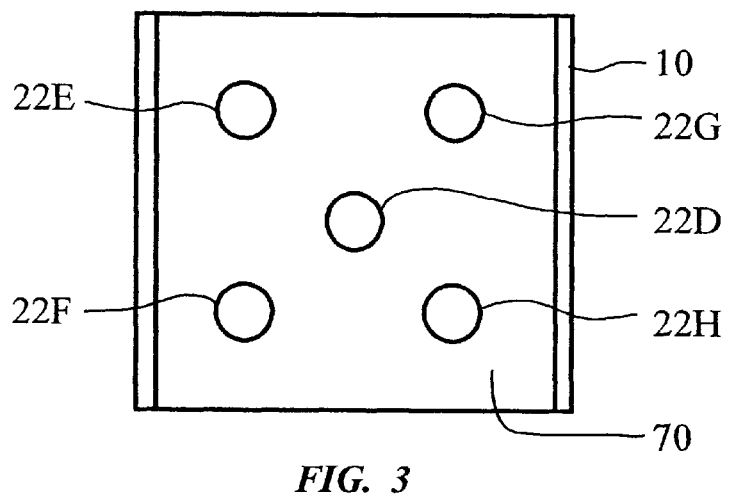
FIG. 3 is a schematic plan view of a testing device of this invention illustrating one pattern for the disposition of a plurality of heat sensing devices above a test specimen.

FIG. 3 depicts one pattern for the disposition of the heat sensing devices above test specimen 70. This pattern which utilizes five heat sensing devices has been found in practice to provide the desired temperature gradient data for test specimens during the tests. It will be seen from FIG. 3 that heat sensing device 22D is substantially centrally disposed above test specimen 70. In the preferred form depicted in FIG. 3, the other four heat sensing devices 22E, 22F, 22G, and 22H, are disposed substantially symmetrically toward the respective corners of the test specimen, and substantially equidistantly from heat sensing device 22D. Here again, if desired, more than five such heat sensing devices can be used for the purpose of establishing the desired temperature gradient data. Likewise, it is possible to use less than five heat sensing devices for this purpose, for example with a circular plate 10 and a circular test specimen 70 (note FIG. 8), but ordinarily this would be a less preferable way to proceed.

Examples of types of heat sensing devices 22 that can be used include thermocouples and thermistors.

Plate 10 can be fabricated of any substance capable of maintaining its structural integrity at temperatures at least as high as the maximum temperature produced by the heater, and capable of transferring heat from its lower surface to its upper surface without excessive reduction in the temperature at its upper surface. As indicated above, the temperatures applied to the test specimen preferably should reach at least as high as about 1600° F. (870° C.) or even higher. Accordingly, plates fabricated from metals or metal alloys satisfying these criteria, such as steel, can be employed. The upper surface of plate 10 can be completely flat, flat with grooves in one direction, flat with grooves at right angles in the form similar to a waffle iron pattern, or the like.

Figure 4:
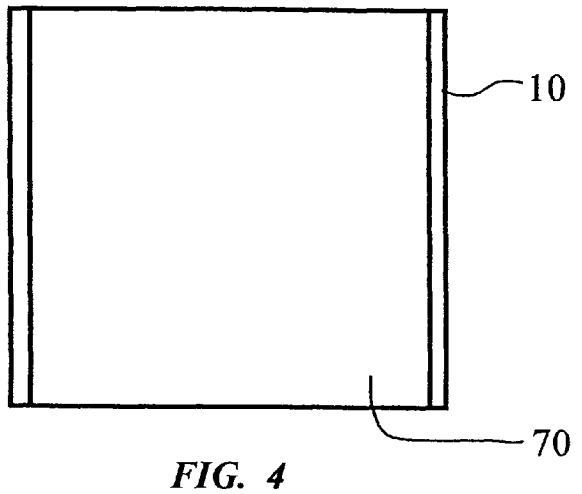
FIG. 4 schematically depicts a test specimen composed of one test piece disposed on the upper surface of a plate in a preferred manner.

Test specimen 70 can be of various configurations in plan view. As can be seen from FIGS. 4, 5, and 6, when using a preferred square plate 10, the test specimen 70 is preferably in the form of one square piece, or two rectangular pieces 70A,70B abutting each other to form a square, or four abutting square pieces 70C,70D,70E,70F arrayed as a square. In one preferred apparatus, plate 10 is equal to or slightly larger than a 2'×2' square. Specimen 70 in the form of one test piece used with such preferred square plate is preferably about 2'×2' square. If test specimen 70 in the form of test pieces 70A and 70B as in FIG. 5 is used with such square plate, each of 70A and 70B is an approximately 1'×2' rectangular piece, whereas if test specimen 70 in the form of test pieces 70C, 70D, 70E, and 70F as in FIG. 6 is used with such square plate, each of 70C, 70D, 70E, and 70F is an approximately 1'×1' square piece.

Figure 7:
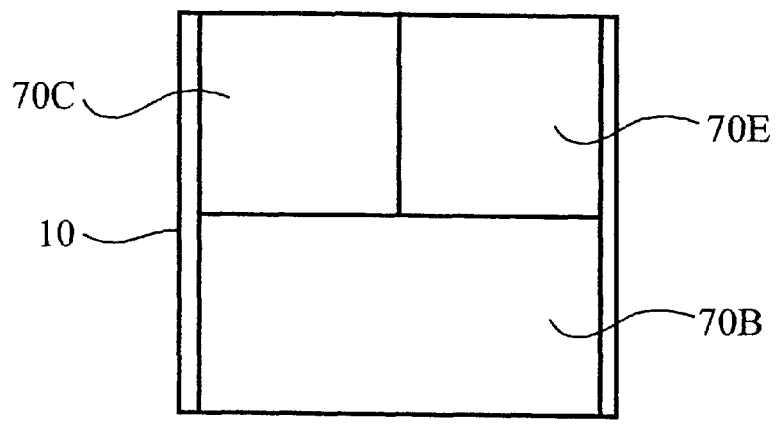
FIG. 7 schematically depicts a test specimen composed of three separate test pieces butted together and disposed on the upper surface of a plate.
Figure 8:
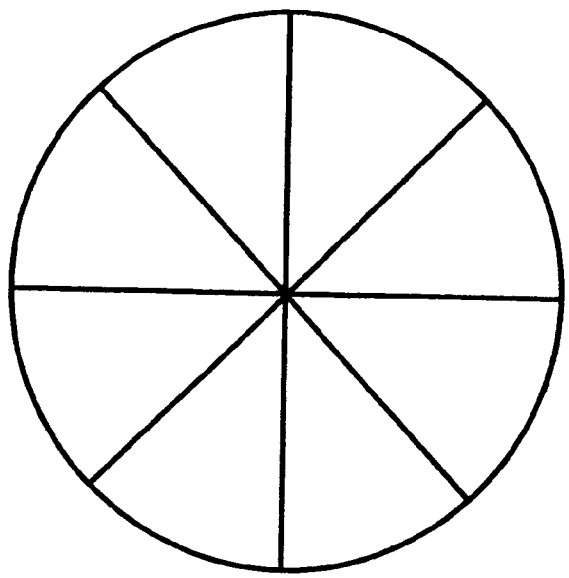
FIG. 8 schematically depicts a test specimen composed of eight separate test pieces butted together and disposed on the upper surface of a plate.

It will be understood and appreciated that other configurations of the test specimen can be used. For example if using a 2'×2' or slightly larger square plate 10, it is possible to use a rectangular piece 1'×2' and two abutting 1'×1' square test pieces aligned along and abutting a 2' side of the rectangular piece to thereby form a 2'×2' square test specimen as depicted in FIG. 7. Indeed, it is possible to employ specimens composed of pieces derived by cutting, say, a square specimen into a variety of abutting pieces, triangular, circular, etc., that fit together when reassembled to abut each other in their original places to reform the original square pattern. The same is true in the case, say, of a circular test specimen which, for example, can be composed of abutting pie-shaped pieces arrayed to form a circle, such as is depicted in FIG. 8. Such a test specimen would preferably be used with apparatus having a circular plate of the same or slightly larger size.

Figure 5:
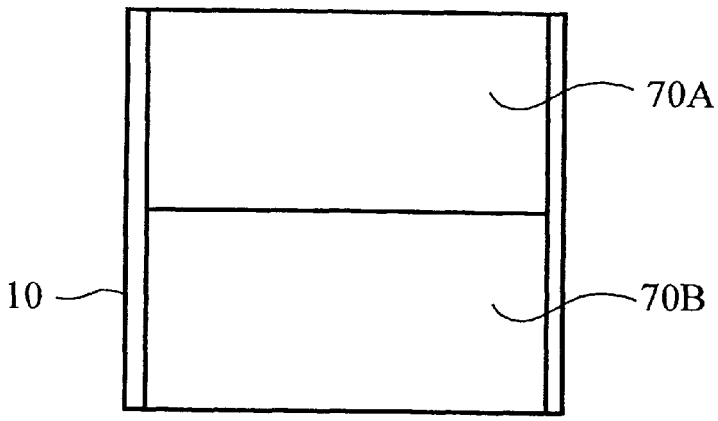
FIG. 5 schematically depicts a test specimen composed of two separate test pieces butted together disposed on the upper surface of a plate disposed in a preferred manner.
Figure 6:
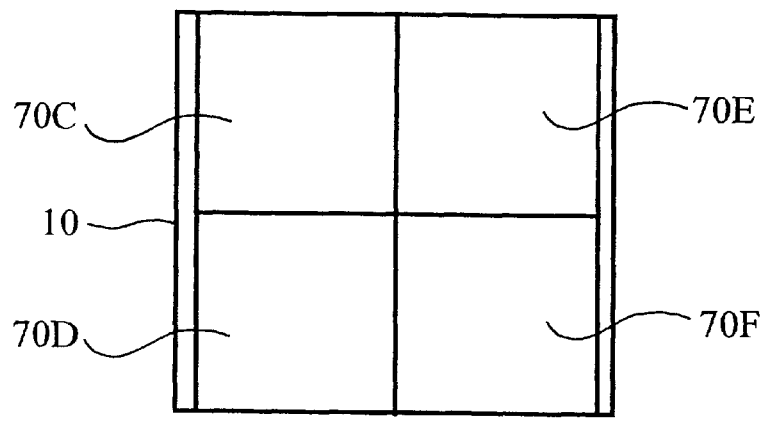
FIG. 6 schematically depicts a test specimen composed of four separate test pieces butted together and disposed on the upper surface of a plate in a preferred manner.

For best results, when test specimen 70 is in the form of two or more pieces such as in FIGS. 5 or 6, or in other configurations in plan view as described above, the test pieces preferably each have approximately the same height. The test pieces should abut each other at their adjacent sides so as to minimize seepage of molten material during the test. Pieces making up a test specimen can be cut from different portions of foam insulation to thereby assess the uniformity of flame retardant dispersal and performance throughout the insulation.

Heater 20 can be any heater capable of achieving temperatures above about 455° C. (850° F.), and preferably at least about 870° C. (1598° F.), and most preferably still higher temperatures. Preferred from the standpoint of safety are electric heaters, and especially radiant ceramic fiber electric heaters. Ceramic fiber heaters utilize suitable heating coils such as iron-chrome-aluminum heating element wire and ceramic thermal insulation material such as ceramic fiber insulation. The wires, such as wire coils, are contained or embedded in the ceramic insulation material. The wire coils may be surround on the sides and bottom by ceramic insulation and covered at the top by a heat stable heat-transmittable plate such as a plate made from a glass having such thermal properties. Watlow Electric Manufacturing Company, 12001 Lackland Road, St. Louis Mo. 63146 produces a number of ceramic heaters for radiant heating applications that are capable of achieving the desired high temperatures for use in the practice of this invention. Watlow Electric heater, Code No. VF16A18T, type 6, 20×22", and 5750W at 240V has been utilized with great success in apparatus of this invention.

Figure 9:
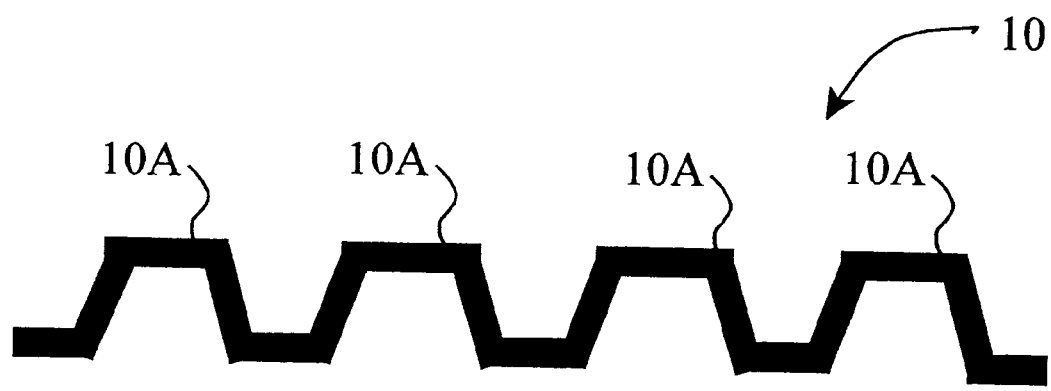
FIG. 9 is a view, in vertical section, of a preferred plate configuration.

FIG. 9 depicts in frontal cross-section a preferred configuration for plate 10 especially when using an essentially square plate, such as an approximately 2×2' essentially square plate. This configuration is that of conventional fluted steel roof decking. The top surfaces 10A are approximately 3.75 inches in width and run approximately 2 feet from front to back thus providing ample surface area upon which the test specimen, can rest. Also the valleys between these top surfaces provide space for seepage or other debris to accumulate during the test. After several tests the zinc coating on the decking is dissipated. Use of an approximately 2×2' essentially square plate, which preferably has this cross-sectional configuration, enables use of a square test sample of essentially the same size, and this in turn facilitates the testing of production foam boards and evaluation of the effects of knit-lines and edges.

Figure 10:
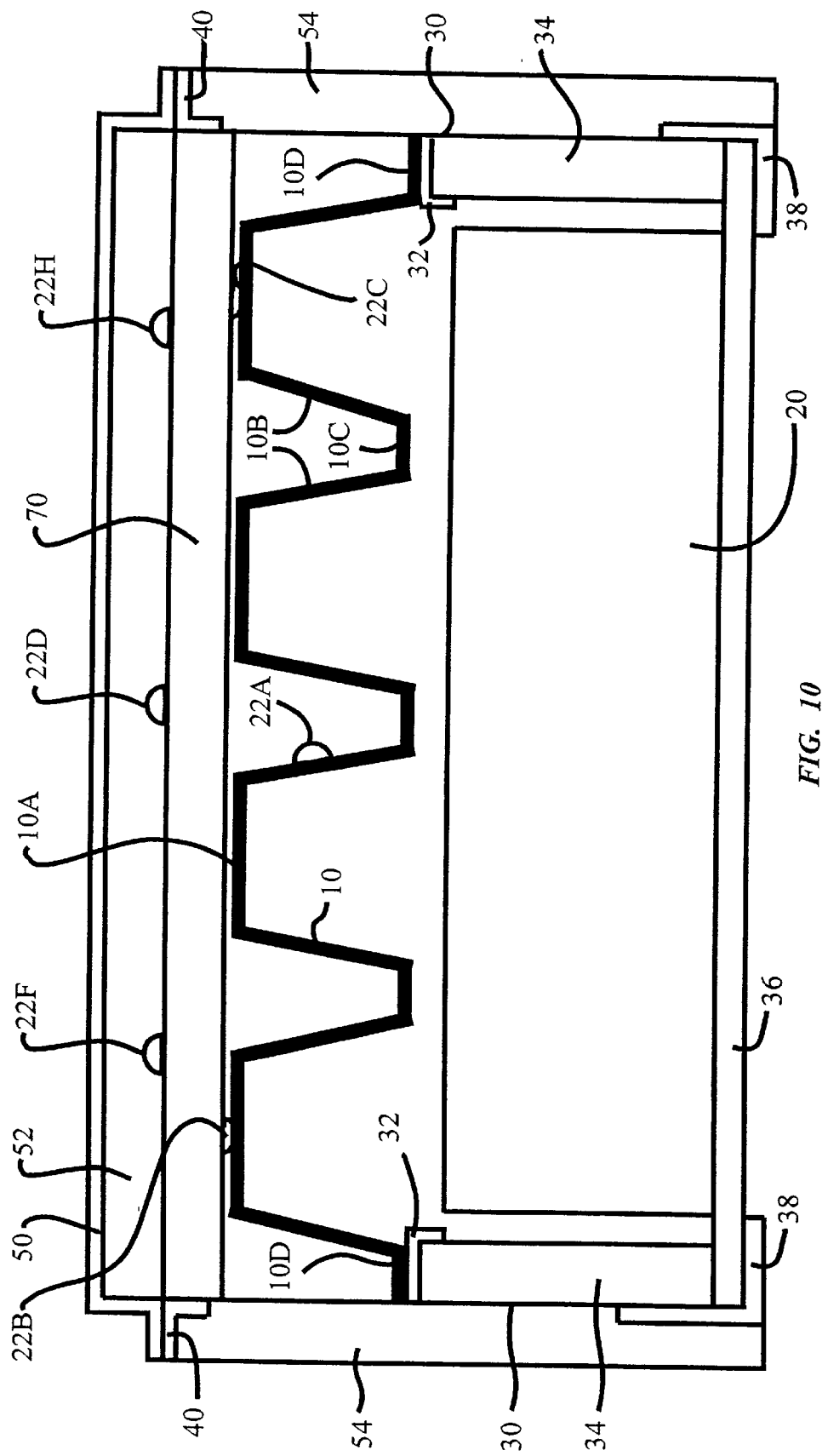
FIG. 10 is a frontal view in section of a preferred testing apparatus of this invention.

Referring now to FIG. 10, which is a frontal section view, the lower portion of the particular preferred apparatus depicted includes wall 30, shelf 32, insulation panel 34, base panel 36, and base support 38. Wall 30, preferably composed of ⅛-inch thick stainless steel plate, defines an enclosed interior space in the apparatus around the perimeter of the elements disposed within that space. In the preferred form depicted, shelf 32 is a right angle iron welded or otherwise affixed to wall 30 with one of the sides of shelf 32 spaced apart from wall 30 and extending downwardly, and base support 38 is another right angular metal strip with one of its sides abutting and affixed to the lower interior of wall 30 with the other side of base support 38 extending inwardly. Plate 10, which preferably is a 2'×2' section of 18 to 26 gauge fluted steel roof decking, rests upon and thus is supported by shelf 32. Similarly, base panel 36 which preferably is a ¼" thick cement board and which preferably encloses the entire bottom area of the apparatus, rests upon and is supported and held in place by base support 38. Shelf 32 and base support 38 can and preferably do, but need not, extend around substantially all interior sides of wall 30. It will be noted that in the form and disposition depicted, shelf 32 performs a dual function. In addition to supporting plate 10, which can be affixed thereto, shelf 32 serves as a retainer for insulation panels 34. Insulation panel 34 preferably extends around the entire inner periphery of wall 30 and may be in the form of a single continuous folded panel or in the form of, say, four abutting panels, one disposed on each of the four sides of wall 30. Panel 34 is preferably fabricated from a ceramic thermal insulation material.

As noted above, the preferred plate 10 is a section such as a 2'×2' square section of 22 to 24 gauge fluted steel roof decking configured as depicted in FIGS. 9 and 10. Whatever the size used, the plate in this configuration should have a plurality of raised flat top surfaces 10A running from front to back (or from side to side if plate 10 is oriented in this manner). In addition plate 10 in this configuration will have at least two grooves between the flat top surfaces extending in the same manner. As depicted each of these groves typically will be defined by two inwardly sloping walls 10B and a lower flat bottom 10C. Also as depicted, the two outer edges of such plates will preferably have on each side running from front to back (or from side to side if plate 10 is oriented in this manner) a flat bottom linear area 10D such as formed by cutting the plate along the a lower flat bottom zone 10C. In the preferred 2'×2' square configuration of this type each of the four top surfaces 10A are 3.75 inches wide and each of the three lower flat bottom zones 10C between the top surfaces is 1.5 inches wide.

Centrally enclosed within the area defined by wall 30 and resting upon base panel 36 is heater 20. In the preferred form the heater is a ceramic fiber heater shaped in the form of a flat panel with coils embedded in the upper surface and arrayed and glass-covered as in Watlow Electric heater, Code No. VF16A18T, type 6, 20×22", and 5750W at 240V. Other suitable heaters can of course be employed. A supply of electric power of appropriate voltage (not shown) is provided to heater 20.

In the preferred form depicted in FIG. 10, the space between the top of heater 20 and the underside of flat bottom zones 10C is essentially ¾ inch.

Along the upper outer perimeter of wall 30 is welded or otherwise affixed, flanged support 40 which in the form depicted is a right angular strip. The side of the strip not affixed directly to wall 30 extends outwardly to provide a flat flange on at least the front and two sides of wall 30. Cover 50 is recessed and is hinged on the back section of wall 30 in any suitable manner so that the cover can be raised to provide easy access to the entire top of plate 10, and lowered to provide an encased space between the cover and the top surfaces 10A of plate 10. Cover 50 is preferably fabricated from a suitable material having thermal insulation properties, such as ¼-inch cement board which can be coated on its top side if desired. As depicted in FIG. 10, cover 50 is insulated with ceramic thermal insulation 52 fitted into and affixed to the interior of the recess. Such insulation should have a thickness of at least about ½-inch. The exterior of wall 30 is also thermally insulated around its entire outer perimeter by ceramic insulation 54 which can be affixed directly on the outer surfaces of wall 30 or held in place by an outer wall (not shown) spaced apart from, but extending around all of, wall 30. The upper portion of insulation 54 should extend upwardly from the bottom of the apparatus up to at least the underside of flanged support 40 (as shown).

In the preferred form of FIG. 10, eight thermocouples disposed as in FIGS. 2 and 3 serve as the heat sensing devices. Each thermocouple is connected by wires to a microprocessor/display device (not shown), such as a conventional personal computer programmed with a suitable program which converts the signals into temperature information, such as a "GeniDAQ" program, a software program available from Advantech Company, Ltd., 1320 Kemper Meadow Drive, Suite 500, Cincinnati, Ohio, 45240. Thus heat sensing device 22A, the control or set-point temperature sensor, is attached to a sloped wall of the central groove depicted, whereas the other two sensors 22B and 22C are laterally spaced apart from device or sensor 22A in contact with a top surface of plate 10 in very close proximity to the bottom of test specimen 70. Visible in FIG. 10 are heat sensing device 22D, substantially centrally disposed above test specimen 70, and two of the other four heat sensing devices, viz., sensors 22F and 22H. The other two sensors 22E and 22G are substantially to the rear of sensors 22F and 22H, respectively, and thus are not visible in FIG. 10.

The height (depth) of the recess in cover 50 should be sufficient to enable the cover, containing insulation 52 and heat sensing devices 22D, 22E, 22F, 22G, and 22H, to be closed over a 4-inch high (thick) test specimen 70 on plate 10 with the specimen completely encased between the top of the plate and the underside of the closed cover. Preferably, these heat sensing devices are supported in position by the thermal insulation 52 with the associated wiring extending laterally in or above insulation 52 and through apertures or small recesses (not shown) in the back wall of cover 50.

The signals from the respective heat sensing devices are typically transmitted to a microprocessor which is adapted to convert such signals into signals corresponding to temperatures sensed by the respective sensing devices. These latter signals in turn are transmitted to a display device adapted to receive the signals from said microprocessor and to display information indicative of the respective temperatures sensed by the respective sensing devices. The display can be in various forms such as for example a printout of numerical data, a continuous strip chart graphically depicting temperatures by lines on a continuous grid, or data recorded on discs or tapes for concurrent and subsequent display. The microprocessor and the display device can be in the form of separate units or a single unitary piece of equipment. Details concerning the makeup and construction of suitable microprocessors and display devices are well known, and such equipment is readily available in the marketplace.

A preferred way in which the test can be conducted pursuant to this invention and the data and observations are used will now be illustrated with reference to preferred apparatus of this invention such as depicted in FIG. 10. After placing test specimen 70 on plate 10, with the heat sensors in place, cover 50 is closed. Heater 20 and the microprocessor and display device are turned on. The particular ceramic fiber heater used is capable in the apparatus depicted of heating the test specimen to 870° C. (1600° C.) or higher within a few minutes. After a preselected temperature, typically at least about 700° C., and preferably in the range of about 825° C. to about 875° C. is reached, the time required for the top-side temperatures to rise to high temperatures is noted and used as an indication of foam char integrity. Averaging the plurality (preferably five) top heat sensor readings minimizes the effect of localized cracks. The time for top side temperatures to reach a preselected temperature such as 260° C. (5000° F.) can also be used for this purpose. After turning off the heater, the cover is raised and unless the specimen is suitably flame retarded, the test specimen in many cases will burst into flame in its central area. Such fire should of course be extinguished without further damaging the remains of the specimen.

Additional data is available from physical inspection of post-test specimens. At least one, and preferably all, of char thickness, weight retention (i.e., difference in weight before and after the test), severity of cracking, and specimen shrinkage, if any, can be, and preferably are, measured. The weight retention and thickness retention data from the test have agreed well with results obtained on specimens of the same foam in the actual standard Calorimeter used in the Factory Mutual 4450/4470 Procedure. In addition, and very significantly, flame retardants and foam formulations that give the best performance in the test method of this invention have also given exceptionally favorable physical results in the Calorimeter. For example, recent Calorimeter testing of 1.5-inch PIR foam made with Saytex XP-4020 flame retardant combination (Albemarle Corporation) gave increased thickness retention and reduced lateral shrinkage, and exhibited minimal opening of the main seam on the test deck, compared to tri(chloroisopropyl) phosphate control as predicted by tests conducted pursuant to this invention.

Except as maybe expressly otherwise indicated, the article "a" or "an" if and as used herein is not intended to limit, and should not be construed as limiting, a claim to a single element to which the article refers. Rather, the article "a" or "an" if and as used herein is intended to cover one or more such elements, unless the text expressly indicates otherwise.

It will also be understood that the terms "essentially" and "substantially" denote that the subject matter referred to need not involve absolutes. For example, instead of describing a variable shape as a "square", it is more realistic to describe the shape as "essentially square" as in the practice of this invention it normally makes little if any difference whether the shape in plan view is a true square or is suitably close to being a true square. Similarly, in most cases it is more realistic to have something "substantially aligned" since in the practice of this invention, micrometer alignment is not necessary; tolerances typically exist. Since the words "essentially" and "substantially" are words in common usage and that are well-defined in the dictionary, they are deemed sufficiently precise and are thus used herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method of testing flammability characteristics of a cellular plastic, which method comprises:
   a) applying heat to the underside of a heat-conductive plate on which are disposed (i) a test specimen of the cellular plastic having a top surface and a bottom surface, (ii) a plurality of spaced-apart heat sensing devices disposed below the specimen and in direct or substantially direct contact with the plate, one said heat sensing device being substantially centrally disposed relative to the plate and serving as the setpoint sensor, and (iii) a plurality of spaced-apart heat sensing devices disposed above the specimen and in direct or substantially direct contact with the top surface of the specimen, one said heat sensing device being substantially centrally disposed relative to the top surface of the specimen, said sensing devices being adapted to provide signals convertible into information regarding the temperatures at their respective locations; and b) at a preselected elevated temperature as sensed by said setpoint sensor, determining the time for the sensors of (iii) to sense a rise in temperature and/or to reach a preselected temperature at or below the preselected elevated temperature sensed by said setpoint sensor, to thereby test flammability characteristics of the cellular plastic.

2. A method of claim 1 wherein the temperature of the test specimen is raised to at least 700° C., and wherein one or more physical properties of the specimen are inspected after completion of the test.

3. A method of claim 2 wherein the one or more inspected physical properties comprise at least one of (a) char thickness, (b) weight retention, (c) severity of cracking, and (d) specimen shrinkage, if any.

4. A method of claim 1 wherein said test specimen is composed of a single piece of said cellular plastic or a plurality of laterally disposed pieces of said cellular plastic arrayed so that each piece abuts at least one other piece, said piece or pieces occupying the entire top surface, or at least substantially the entire top surface, of the plate.

5. A method of testing flammability characteristics of a cellular plastic, which method comprises:

a) placing (i) a test specimen of cellular plastic having upper and lower surfaces, each surface having a central location, on (ii) a heat-conductive plate having upper and lower surfaces, each surface having a central location, said specimen being disposed with the central locations of the specimen substantially aligned with the central locations of the plate, and with (iii) a plurality of spaced-apart heat sensing devices disposed below the specimen and in direct or substantially direct contact with the plate, one said heat sensing device being centrally or substantially centrally disposed relative to the central location of the plate and serving as the setpoint sensor, and (iv) a plurality of spaced-apart heat sensing devices disposed above the specimen and in direct or substantially direct contact with the top surface of the specimen, one said heat sensing device being centrally or substantially centrally disposed relative to the central location of top surface of the specimen, said sensing devices being adapted to provide signals convertible into information regarding the temperatures at their respective locations;

b) applying heat to the lower surface of the plate below a substantially uniform area around the central locations of the plate and of the test specimen so that the temperatures of the plate and the specimen are raised high enough to cause degradation of the specimen to commence and progress; and c) recording the temperatures at the respective locations of the heat sensing devices, thereby enabling correlation between degradation and/or flammability properties of the specimen and temperatures at the locations of the heat sensing devices.

6. A method of claim 5 wherein the temperature of the test specimen is raised to at least 700° C., and wherein one or more physical properties of the specimen are inspected after completion of the test.

7. A method of claim 6 wherein said test specimen is composed of a single piece of said cellular plastic or a plurality of laterally disposed pieces of said cellular plastic arrayed so that each piece abuts at least one other piece, said piece or pieces occupying the entire top surface, or at least substantially the entire top surface, of the plate; and wherein the one or more inspected physical properties comprise at least one of (a) char thickness, (b) weight retention, and (c) severity of cracking.

8. A method of any of the preceding claims wherein said plate and said specimen are entirely or substantially entirely within the confines of a thermally insulated housing at least during the heating.

9. Apparatus adapted for testing flammability characteristics of a cellular plastic, which apparatus comprises:

a) a heat-conductive plate having upper and lower surfaces, each surface having a central location;

b) a heater centrally or substantially centrally disposed relative to said central locations of the plate;

c) a plurality of heat sensing devices adapted, when a specimen of a cellular plastic is placed on said plate, to be disposed in spaced-apart locations below the test specimen and in direct or substantially direct contact with the plate, and to transmit signals convertible into information regarding the temperature at the location of the heat sensing device;

d) a plurality of spaced-apart heat sensing devices adapted, when a specimen of a cellular plastic is placed on said plate, to be disposed in spaced apart locations above the specimen and in direct or substantially direct contact with a top surface of the specimen, and to transmit signals convertible into information regarding the temperature at the location of the heat sensing device;

e) a thermally insulated housing including a thermally insulated cover, said housing and said cover when closed being adapted to encase said plate, a specimen of a cellular plastic when placed on said plate, and said heater entirely or substantially entirely within the confines of said housing and cover;

f) a microprocessor adapted to receive signals from the respective heat sensing devices, and to convert said signals into signals corresponding to temperatures sensed by the respective sensing devices; and g) a display device, adapted to receive the signals from said microprocessor and to display information indicative of the respective temperatures sensed by the respective sensing devices;

wherein f) and g) can be separate units or a single combined unit.

10. Apparatus of claim 9 wherein said heater is a thermally insulated radiant heater capable of heating test samples through the plate to temperatures of up to about 870° C. (1600° F.) or higher, and wherein said heat sensing devices are thermocouples.

* * * * *

UNITED STATES PATENT AND TRADEMARK OFFICE
CERTIFICATE OF CORRECTION

PATENT NO. : 6,536,943 B1
DATED : March 25, 2003
INVENTOR(S) : Elbert F. Feske

It is certified that error appears in the above-identified patent and that said Letters Patent is hereby corrected as shown below:

Column 11,
Line 7, reads "sensor, to thereby..." and should read -- sensor, (Paragraph Break) to hereby... --

Signed and Sealed this

Eighth Day of March, 2005

JON W. DUDAS
*Director of the United States Patent and Trademark Office*